United States Patent [19]

van Andel

[11] Patent Number: Plant 5,505

[45] Date of Patent: Jul. 2, 1985

[54] CARNATION NAMED MULOPI

[75] Inventor: Jacob van Andel, Aalsmeer, Netherlands

[73] Assignee: B. V. Handelskwekerij, M. V. van Staaveren, Aalsmeer, Netherlands

[21] Appl. No.: 556,457

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new and distinct variety of miniature carnation characterized by its fast and profuse production of small flowers having white bodied petals edged and marginally striped with a violet red color, the plant being particularly distinguished by the larger number of flowers borne on each flowering stem.

1 Drawing Figure

BACKGROUND OF THE NEW PLANT

This new miniature carnation plant originated as a seedling of unknown parentage growing among a collection of miniature carnation plants maintained in greenhouse for breeding purposes at Aalsmeer, Holland, this particular plant being selected by me for propagation and test because of its profuse production of miniature flowers having a very unusual coloration. I propagated this discovery plant by means of cuttings at Aalsmeer and the results were so favorable that I continued propagation through several successive generations and thereby determined not only the growth and flowering characteristics of the plant but also that these distinctive features would hold true from generation to generation and appeared to be firmly fixed.

DESCRIPTION OF THE DRAWING

My new variety of miniature carnation is illustrated by the accompanying full color photographic drawing which shows several flower stems of the plant together with buds in various stages of growth and opening, together with newly opened and fully opened flowers, the colors being as nearly true as it is reasonably possible to obtain by conventional photographic procedures.

DESCRIPTION OF THE NEW PLANT

The following is a detailed description of my new variety of miniature carnation plant as observed in greenhouse in the early Summer of 1983 with color designations according to The R.H.S. Colour Chart published by The Royal Horticultural Society of London, England.

THE PLANT

Origin: Seedling.
Parentage:
- *Seed parent.*—Unknown.
- *Pollen parent.*—Unknown.

Classification:
- *Botanic.*—*Dianthus caryophyllus* Hybrid.
- *Commercial.*—Miniature carnation for cut flowers.

Form: Tall bush.
Height: Various depending on season.
Growth: Vigorous, strong and upright with normal branching.
Foliage:

- *Quantity.*—Medium.
- *Size of leaf.*—Medium and of oblong shape.
- *Texture.*—Smooth.
- *Color.*—Upper side — Grey/Green. Under side — Grey/Green.
- *Petioles.*—None. The leaf is sessile.

THE BUD

Form: Pointed ovoid, becoming cylindrical upon reaching the stage of dividing sepals.
Size: Medium.
- *Diameter.*—About 10 mm.
- *Length.*—About 30 mm.

Rate of opening: Moderate.
Color of petals.
- *When sepals begin to divide.*—Outside White edged with Purple.
- *When sepals begin to unfurl.*—Top side White edged with Purple, many with many Purple stripes at outer end of petals.

Sepals:
- *Shape.*—Oblong with acute apex. Sepals stand up when flowers open.
- *Color.*—Inside — Grey/Green. Outside — Grey/-Green .

Calyx:
- *Shape.*—Funnel-shaped.
- *Size.*—Medium.
- *Aspect.*—Smooth.
- *Splitting.*—The calyx does not split.

Flower stem:
- *Character.*—Long and erect.
- *Color.*—Grey/Green.

THE FLOWER

Blooming habit: Continuous and profuse.
Size of bloom: Small.
- *Diameter.*—About 40 mm.
- *Depth.*—About 20 mm.

Shape:
- *When bloom first opens.*—High centered.
- *When bloom matures.*—All petals open out and spread.

Petalage:
- *Number of petals.*—About 30.
- *Arrangement.*—Spreading and overlapping.
- *Form.*—Fan-shaped with serrated margin.
- *Texture.*—Soft.

*Appearance.*—Shiny.

*Color.*—All Petals: Top side — White, R.H.S. 155D, edged with Violet Red. Base — Pale Green. Reverse side — White, R.H.S. 155D, edged with Violet Red.

Fragrance: Weak to medium.

Persistence: The flowers hang on and dry.

Disease resistance: The flowers are less susceptible to fusarium oxysporum as observed in the Aalsmeer area of The Netherlands.

Lasting quality:

*On plant.*—About 20 days.

*As cut flower.*—About 10 to 14 days.

REPRODUCTIVE ORGANS

Stamens:

*Number.*—Medium.

*Anthers.*—Size: Medium. Color: Cream.

*Filaments.*—Color: White.

*Pollen.*—Color: Cream/Yellow.

Pistils:

*Number.*—One.

*Style.*—Length: Approximately 25 mm. Color: White.

*Stigma.*—Color: White.

This miniature carnation is of a new type and compared with the common miniature variety, this type has a greater number of smaller flowers per flower stem, a well as a fast and profuse production of blooms.

I claim:

1. A new and distinct miniature carnation cultivar, substantially as herein shown and described, characterized by its fast and excellent production of blooms with a larger than normal number of flowers on each flowering stem.

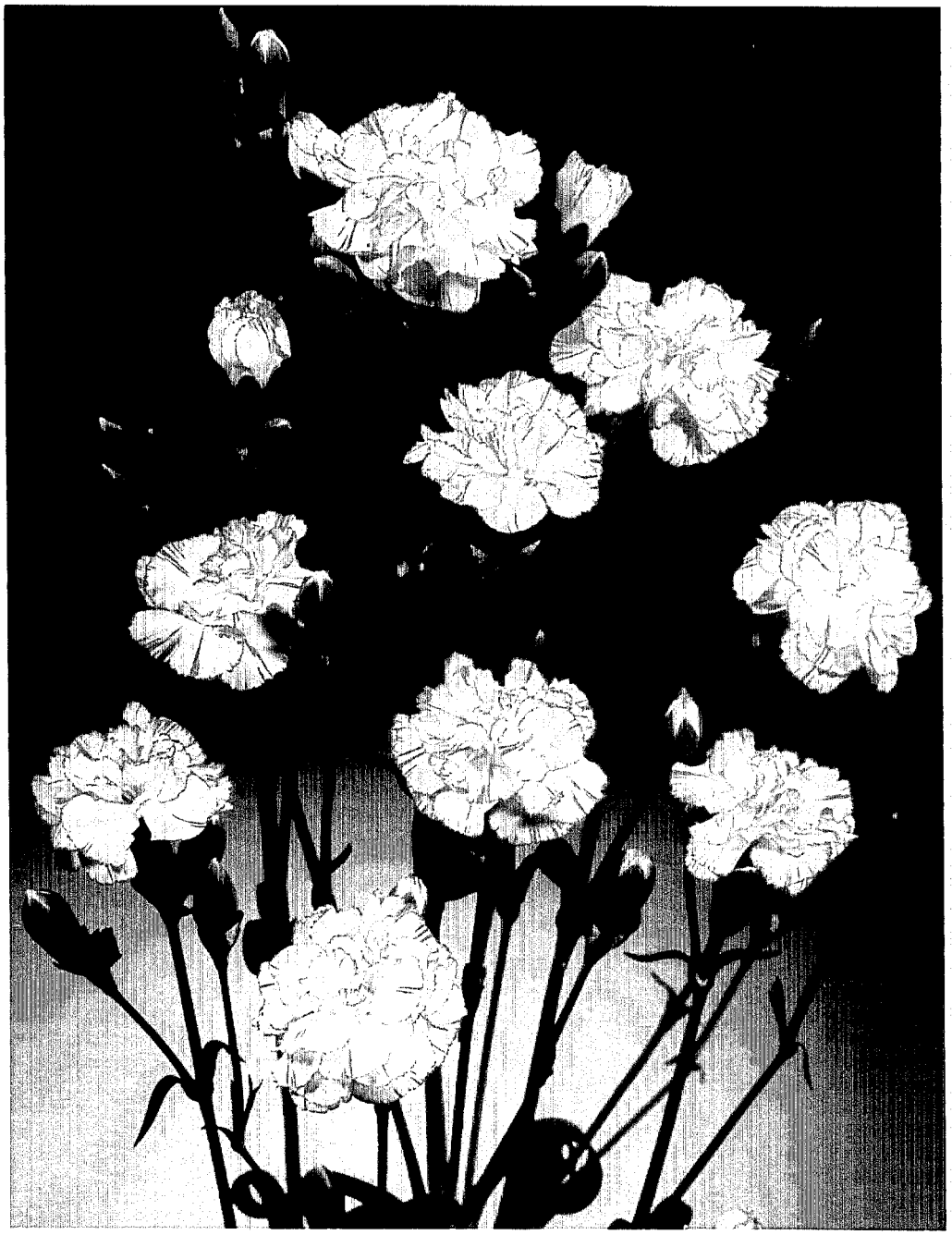

* * * * *